(12) United States Patent
Lee et al.

(10) Patent No.: US 12,324,482 B2
(45) Date of Patent: Jun. 10, 2025

(54) SELF-GENERATING AND VIBRATING FUNCTIONAL SHOE EQUIPPED WITH GPS DEVICE

(71) Applicant: SHOEALLS CO., LTD., Cheonan-si (KR)

(72) Inventors: Cheong Geun Lee, Cheonan-si (KR); Byeong Am Bae, Busan (KR)

( * ) Notice: Subject to any disclaimer, the term of this patent is extended or adjusted under 35 U.S.C. 154(b) by 0 days.

(21) Appl. No.: 18/549,655

(22) PCT Filed: Nov. 1, 2022

(86) PCT No.: PCT/KR2022/016866
§ 371 (c)(1),
(2) Date: Sep. 8, 2023

(87) PCT Pub. No.: WO2023/120949
PCT Pub. Date: Jun. 29, 2023

(65) Prior Publication Data
US 2024/0156205 A1    May 16, 2024

(30) Foreign Application Priority Data
Dec. 24, 2021  (KR) .................. 10-2021-0187523

(51) Int. Cl.
*A43B 3/42*  (2022.01)
*A43B 3/44*  (2022.01)
(Continued)

(52) U.S. Cl.
CPC .................. *A43B 3/42* (2022.01); *A43B 3/44* (2022.01); *A43B 3/46* (2022.01); *A43B 3/48* (2022.01);
(Continued)

(58) Field of Classification Search
CPC .... A43B 3/42; A43B 3/44; A43B 3/48; H02K 7/1853; H02K 7/1861; H02N 11/002; A61B 5/6807; A61B 2560/0214
See application file for complete search history.

(56) References Cited

U.S. PATENT DOCUMENTS

| | | | | |
|---|---|---|---|---|
| 1,506,282 A | * | 8/1924 | Barbieri | A43B 3/35 74/130 |
| 4,674,199 A | * | 6/1987 | Lakic | A43B 3/38 36/2.6 |

(Continued)

FOREIGN PATENT DOCUMENTS

| | | | | |
|---|---|---|---|---|
| CN | 106899233 A | * | 6/2017 | H02K 35/02 |
| CN | 213849039 U | * | 8/2021 | A43B 7/14 |

(Continued)

*Primary Examiner* — Pedro J Cuevas
(74) *Attorney, Agent, or Firm* — KORUS Patent, LLC; Seong Il Jeong

(57) ABSTRACT

The present invention relates to a functional shoe configured to generate power when a user wearing the shoe walks, so that a battery there inside can be charged, and to supply the charged electricity to internal and external devices so as to be used for the purpose of user safety and device charging, and enable use of a location tracking function using a GPS device. A self-generating smart shoe according to the present invention comprises: an outsole constituting the lower portion of the shoe while having a plurality of receiving portions formed therein; a self-generation unit which, while being installed at the heel of the outsole, generates power by using a pressure generated when the user wearing the shoe walks and the restoring force due to the pressure; and a battery which, while being installed in the outsole, is charged when the self-generation unit generates power.

4 Claims, 4 Drawing Sheets

(51) Int. Cl.
*A43B 3/46* (2022.01)
*A43B 3/48* (2022.01)
*H02J 7/00* (2006.01)
*H02K 7/18* (2006.01)
*H02N 11/00* (2006.01)
*H04W 4/14* (2009.01)

(52) U.S. Cl.
CPC .......... *H02J 7/0042* (2013.01); *H02K 7/1853* (2013.01); *H02K 7/1861* (2013.01); *H02N 11/002* (2013.01); *H04W 4/14* (2013.01)

(56) References Cited

U.S. PATENT DOCUMENTS

| | | | | |
|---|---|---|---|---|
| 4,782,602 A * | 11/1988 | Lakic | ................ | A43B 13/203 36/2.6 |
| 4,845,338 A * | 7/1989 | Lakic | ................ | A41D 19/001 36/2.6 |
| 5,495,682 A * | 3/1996 | Chen | ................ | A43B 3/35 36/137 |
| 6,255,799 B1 * | 7/2001 | Le | ................ | H02J 7/1415 320/DIG. 34 |
| 6,281,594 B1 * | 8/2001 | Sarich | ................ | A43B 3/35 290/1 R |
| 6,724,105 B2 * | 4/2004 | Chen | ................ | H02K 7/06 310/20 |
| 7,409,784 B2 * | 8/2008 | Yeh | ................ | A43B 3/00 36/137 |
| 7,956,753 B2 * | 6/2011 | Fogg | ................ | G08B 21/22 340/573.1 |
| 8,970,054 B2 * | 3/2015 | Stanton | ................ | F03G 5/06 290/1 C |
| 9,107,468 B1 * | 8/2015 | Xiong | ................ | A43B 3/35 |
| 9,190,886 B2 * | 11/2015 | Stanton | ................ | H02K 7/1853 |
| 9,498,017 B2 * | 11/2016 | Lin | ................ | A43B 3/38 |
| 9,716,419 B2 * | 7/2017 | Stanton | ................ | F03G 5/06 |
| 10,499,703 B2 * | 12/2019 | Sharpes | ................ | A43B 3/38 |
| 10,517,355 B2 * | 12/2019 | Schneider | ................ | A43C 1/00 |
| 11,272,762 B2 * | 3/2022 | Schneider | ................ | B65H 59/00 |
| 11,751,627 B2 * | 9/2023 | Cho | ................ | B06B 1/085 601/46 |
| 2011/0003665 A1 * | 1/2011 | Burton | ................ | G06F 13/4282 482/8 |
| 2012/0260522 A1 * | 10/2012 | Shi | ................ | A43B 7/144 36/2.6 |
| 2013/0219743 A1 * | 8/2013 | Ye | ................ | A43B 13/14 36/2.6 |
| 2013/0247410 A1 * | 9/2013 | Tseng | ................ | A43B 1/0054 36/2.6 |
| 2014/0145450 A1 * | 5/2014 | Stanton | ................ | H02K 7/1853 290/1 C |
| 2016/0310077 A1 * | 10/2016 | Hunter | ................ | G16H 40/60 |
| 2017/0265594 A1 * | 9/2017 | Walker | ................ | A43B 3/44 |
| 2018/0192942 A1 * | 7/2018 | Clark | ................ | A61B 5/1128 |
| 2018/0279714 A1 * | 10/2018 | Deng | ................ | H02J 7/00 |
| 2020/0170515 A1 * | 6/2020 | Wen | ................ | A61B 5/0077 |
| 2020/0359735 A1 * | 11/2020 | Cho | ................ | B06B 1/045 |
| 2023/0371652 A1 * | 11/2023 | Walker | ................ | G05B 15/02 |
| 2024/0016255 A1 * | 1/2024 | Meneau | ................ | A43B 3/44 |
| 2024/0019277 A1 * | 1/2024 | Meneau | ................ | G01R 27/2605 |

FOREIGN PATENT DOCUMENTS

| | | | | |
|---|---|---|---|---|
| CN | 118555925 A * | 8/2024 | .......... | A43B 1/0054 |
| KR | 10-2004-0023848 A | 3/2004 | | |
| KR | 20-2009-007638 U | 7/2009 | | |
| KR | 101158760 B1 * | 6/2012 | .......... | A43B 1/0054 |
| KR | 20150063640 A * | 6/2015 | .......... | A61H 7/005 |
| KR | 10-1602246 B1 | 3/2016 | | |
| KR | 10-2017-0053222 A | 5/2017 | | |
| KR | 10-1827946 B1 | 2/2018 | | |
| KR | 200486537 Y1 * | 5/2018 | .......... | A43B 7/146 |
| KR | 101903704 B1 * | 10/2018 | .......... | A61H 23/00 |
| KR | 102128378 B1 * | 6/2020 | ........ | A61H 23/0218 |
| KR | 102149055 B1 * | 8/2020 | .......... | A42B 7/146 |
| KR | 20210014550 A * | 2/2021 | .......... | A61H 39/04 |
| KR | 102494468 B1 * | 2/2023 | .......... | A43B 3/44 |
| WO | WO-2019142959 A1 * | 7/2019 | .......... | A43B 13/18 |
| WO | WO-2021085907 A1 * | 5/2021 | ........ | A61H 23/0218 |

\* cited by examiner

SELF-GENERATING AND VIBRATING FUNCTIONAL SHOE EQUIPPED WITH GPS DEVICE

TECHNICAL FIELD

The present disclosure relates to a power-generating functional shoe equipped with a GPS device and, more particularly, to a functional shoe configured to generate power when a user wearing the shoe walks, so that a battery thereinside can be charged, and supply the charged electricity to internal and external devices so as to be used for the purpose of user safety and device charging, and enable use of a location tracking function using the GPS device.

BACKGROUND ART

In general, shoes, which are an essential item for human life, are worn for the purpose of protecting the feet from pressure and shock generated when the wearer walks, and to achieve that purpose and to better the effects of the purpose, not only design but also functionality such as light weight, cushioning, ventilation and durability have been emphasized.

Recently, however, going beyond the original purpose of shoes to protect the feet, attempts have been made to use the pressure periodically generated by the wearer's walking for power generation, and as a result, inventions such as Korean Patent No. 10-1602246 "SELF POWER-GENERATING SHOE" and Korean Patent No. 10-1827946 "GENERATOR FOR SHOE" have been proposed and published.

First, the Korean Patent No. 10-1602246 "SELF POWER-GENERATING SHOE" discloses a shoe constructed such that the displacement of a leaf spring in both directions occurs due to the pressure generated when the wearer walks, and when the displacement of the leaf spring occurs, a bar magnet coupled to the leaf spring slides into the inside of a coil and interacts with the coil, so that electricity may be generated with high efficiency just by the wearer's walking, and the generated electricity may be used to charge electrical appliances.

In addition, the Korean Patent No. 10-1827946 "GENERATOR FOR SHOE" discloses a generator constructed such that a drive gear under the sole of the shoe, a bevel gear, a horizontal gear, and a coil core are sequentially driven by the pressure generated when the wearer walks, and the interaction between the coil core and a magnet occurs, so that electricity may be generated just by the wearer's walking, and the generated electricity may be used to charge electrical appliances.

However, in the case of "SELF POWER-GENERATING SHOE" of the above inventions, as the shape of the leaf spring formed with a curved middle is quickly flattened due to repeated pressure, the flow distance of the bar magnet coupled to the leaf spring decreases, resulting in a durability problem that may significantly reduce power generation efficiency.

In the case of "GENERATOR FOR SHOE" of the above inventions, inconvenience in use may occur depending on the position of the drive gear where the pressure caused by the wearer's walking directly acts, and a rather large number of mediums provided for transmitting pressure may reduce durability, increase product size, and increase production costs.

In addition, although a solution has been proposed in which the drive gear is provided on each of the left and right sides of the shoe to solve the problem of inconvenience in use due to the location of the drive gear, the problems of decreased durability, increased product size, and increased production costs may only be exacerbated.

Accordingly, there is a demand for inventions related to shoes equipped with a new power generation device configured to generate power with high efficiency by the pressure generated when a user wearing the shoe walks, and furthermore, to efficiently solve the above-mentioned problems of durability, increase in product size, and increase in production costs.

DISCLOSURE

Technical Problem

The present disclosure has been made keeping in mind the problems occurring in the related art. An objective of the present disclosure is to provide a self power-generating shoe equipped with a vibrating function and a GPS device,
which offers a solution to the problems of decrease in durability, increase in product size, and increase in production costs since such problems occur in the conventional cases configured to generate power using pressure generated when the wearer walks.

Technical Solution

In order to achieve the above mentioned objectives,
according to an embodiment of the present disclosure, there is provided a self power-generating shoe equipped with a vibrating function and a GPS device including: an outsole constituting the lower portion of the shoe while having a plurality of receiving portions formed therein, a self power-generation unit which, while being installed at the heel of the outsole, generates power by using pressure generated when the user wearing the shoe walks and the restoring force due to the pressure, and a battery which, while being installed in the outsole, is charged when the self power-generation unit generates power.

At this time, the self power-generation unit may include: a casing in which a hollow is formed therein; a lifting portion configured to include a cylindrical body with a screw thread formed on an outer periphery thereof, an upper head having a wider width than the body, and a lower spring supporting the body, and move up and down vertically by the pressure and restoring force generated when the user wearing the shoe walks in a state in which the head and a part of the body are installed in the casing in a form protruding outward; a first gear axially rotating in a different direction when the lifting portion moves up and down while being installed inside the casing in a form corresponding to the screw thread of the lifting portion; a gear portion composed of a second gear rotating in correspondence with the first gear and a third gear rotating while connected to the same rotational axis as the second gear; and a generator having a fourth gear, meshing with the third gear, installed at an end of a rotating shaft that rotates an internal coil, so that the generator generates power, while being installed inside the casing, in conjunction with the third gear that axially rotates.

Advantageous Effects

According to a self power-generating shoe equipped with a vibrating function and a GPS device of the present disclosure, by installing a self power-generation unit and battery that generate power by pressure on the outsole of the shoe, the battery can be charged while a user wearing the shoe is walking, and by simplifying the configuration and operation method of the self power-generation unit installed in the outsole, it is possible to guarantee sufficient durability, prevent product size expansion, and reduce production costs compared to the conventional cases devised for the same purpose.

BEST MODE

A self power-generating shoe equipped with a vibrating function and a GPS device according to the present disclosure includes:

An outsole 100 constituting the lower portion of the shoe while having a plurality of receiving portions 110 formed therein;

a self power-generation unit 200 which, while being installed at the heel of the outsole 100, generates power by using pressure generated when a user wearing the shoe walks and the restoring force due to the pressure; and a battery 300 which, while being installed in the outsole 100, is charged when the self power-generation unit 200 generates power.

MODE FOR INVENTION

The present disclosure relates to a functional shoe configured to generate power when a user wearing the shoe walks, so that a battery there inside can be charged, and supply the charged electricity to internal and external devices so as to be used for the purpose of user safety and device charging, and enable use of a location tracking function using the GPS device.

The present disclosure includes an outsole 100 constituting the lower portion of the shoe while having a plurality of receiving portions 110 formed therein; a self power-generation unit 200 which, while being installed at the heel of the outsole 100, generates power by using pressure generated when the user wearing the shoe walks and the restoring force due to the pressure; and a battery 300 which, while being installed in the outsole 100, is charged when the self power-generation unit 200 generates power.

Hereinafter, embodiments of the present disclosure will be described in detail with reference to the accompanying drawings.

First, as described above, the present disclosure is configured to include the outsole 100 constituting the lower portion of the shoe in a state in which the plurality of receiving portions 110 is formed.

Figure 1:
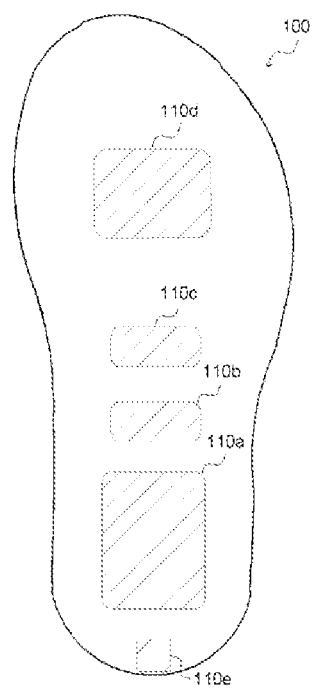
FIG. 1 is a plan view showing a plurality of receiving portions formed on an outsole of a self power-generating shoe equipped with a vibrating function and a GPS device according to the present disclosure.

That is, the outsole 100 is a component of the lower portion of the shoe that directly contacts and rubs against the ground, and, as shown in FIG. 1, since the receiving portions 110 are provided in the form of grooves having different sizes on the outsole, all components of the present disclosure, including the self power-generation unit 200 and the battery 300 to be described later, may be installed inside the shoe.

To be specific, one receiving portion 110a in which the self power-generation unit 200 is installed may be provided on the heel of the outsole 100, another receiving portion 110b in which the battery 300 is installed may be provided on the middle of the outsole 100, and yet another receiving portion 110c in which a multifunction module 400 is installed may be provided at another location of the middle of the outsole 100.

In addition, another receiving portion 110d for installing a vibration terminal 600 may be provided on the front of the outsole 100, and yet another receiving portion 110e for installing a charging port 500 may be provided on the heel.

At this time, each receiving portion 110 provided in the outsole 100 is preferably formed in a size and shape customized to the object to be installed, and the receiving portions 110 except for the receiving portion 110d provided on the front for the purpose of installing the vibration terminal 600 may be connected to one or more other receiving portions 110 through a wiring path for wiring.

Therefore, the outsole 100 is preferably formed with a heel height of 2 cm or more for installation of the self power-generation unit 200 and the like and formation of the wiring path, and is preferably made of PVC or rubber material, which has excellent durability and is not easily worn.

In addition, as previously described, the present disclosure may include the self power-generation unit 200 which, while being installed at the heel of the outsole, repeatedly generates power by using the pressure generated when a user wearing the shoe walks and the restoring force due to the pressure.

That is, the self power-generation unit 200 is a device for power generation that operates by using pressure generated when a user wearing the shoe walks as a driving force, and generates power using pressure, but additionally uses the restoring force caused by the pressure so that repeated power generation may occur by the user's walking.

Figure 2:
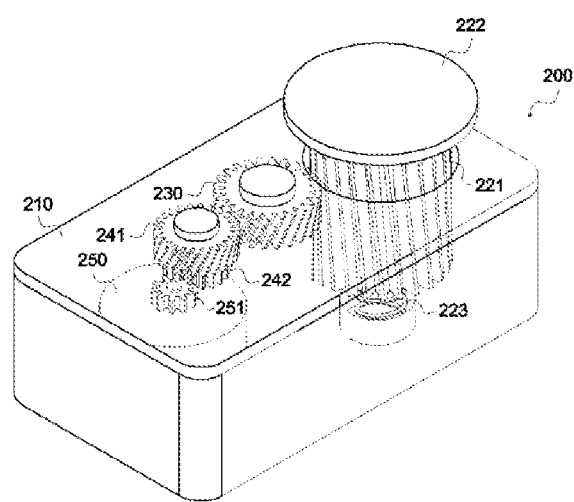
FIG. 2 is a perspective view showing the shape of a self power-generation unit of the present disclosure.

To be specific, as shown in FIG. 2, the self power-generation unit 200 includes: a casing 210 in which a hollow is formed therein; and a lifting portion 220 including a cylindrical body 221 with a screw thread formed on the outer periphery thereof, an upper head 222 having a wider width than the body 221, and a lower spring 223 supporting the body 221. The lifting portion 220 moves up and down vertically by pressure and restoring force generated when the user wearing the shoe walks in a state in which the head 222 and a part of the body 221 are installed in the casing 210 in a form protruding outward.

At this time, the casing 210 has a structure capable of opening and closing the top thereof, and a through hole is formed on one side of the top for protruding part of the lifting portion 220, wherein on one side of the bottom of the casing 210 perpendicular to the through hole, an inlet groove is formed or provided in a form protruding from the bottom of the casing 210 so that the spring 223 may be installed in the inlet groove.

Therefore, the lifting portion 220 may be installed in the casing 210 in a vertical form in which the spring 223 is located at the bottom and the head 222 is located at the top. The lifting portion 220 is configured to be able to repeatedly move up and down without failure due to downward pressure and upward restoring force generated when the user walks.

In the lifting portion 220, the diameter of the head 222 needs to be wider than the diameter of the body 221 or the diameter of the through hole formed at the top of the casing 210, and the contact surface between the lifting portion 220 and an insole inside the shoe should be wide enough to prevent pain or discomfort when the user walks. At the same time, it is necessary to prevent excessive pressure from being applied to the spring 223 by limiting the distance at which the lifting portion 220 can descend.

That is, the head 222 of the lifting portion 220 is a pressing plate pressed by the user's foot while being covered by the insole inside the shoe, and may be used as a holding jaw that is caught on the top of the casing 210 when the lifting portion 220 descends.

In addition, the screw thread is formed on the outer periphery of the body 221 of the lifting portion 220 by taking the width direction of the lifting portion 220 as an axis.

That is, while a normal screw thread is formed in a spiral shape with the longitudinal direction of a bolt or screw as an axis, the screw thread formed on the outer periphery of the lifting portion 220 has a shape formed in a spiral shape in the width direction of the lifting portion 220 as an axis, so that it is possible to transmit external force through lifting instead of the usual method of transmitting external force through rotation.

In addition, as shown in FIG. 2, the self power-generation unit 200 includes: a first gear 230 axially rotating in a different direction when the lifting portion 220 moves up and down while being installed inside the casing 210 in a form corresponding to the thread of the lifting portion 220; a second gear 241 rotating in correspondence with the first gear 230; and a third gear 242 rotating while connected to the same rotational axis as the second gear 241.

At this time, the first gear 230 is composed of an oblique gear, and is installed in a form corresponding to the screw thread formed on the outer periphery of the body 221 of the lifting portion 220 so as to rotate in the forward or reverse direction by the lifting of the lifting portion 220.

The self power-generation unit 200 further includes: a generator 250 having a fourth gear 251, meshing with the third gear 242, installed at the end of a rotating shaft that rotates an internal coil, so that the generator 250 generates power, while being installed inside the casing 210, in conjunction with the third gear 242 that rotates.

At this time, the third gear 242 and the fourth gear 251 are composed of general toothed gears, and are installed in a form corresponding to each other so as to rotate in opposite directions.

That is, the self power-generation unit 200 is configured such that the lifting portion 220 temporarily descends by the pressure generated when the user walks and rotates the first gear 230, and as the first gear 230 rotates, a gear portion 240 rotates in a chain, and as the gear portion 240 rotates, the fourth gear 251 rotates in a chain, and as a result, a rotor inside the generator 250 is axially rotated.

At this time, it is preferable that the body 221 of the lifting portion 220 the first gear 230, the gear portion 240, and the fourth gear 251 are configured such that their diameters gradually decrease according to the transmission order of power when the lifting portion 220 descends, so that the number of rotations gradually increases, and the amount of power generated by the generator 250 increases as the number of rotations increases.

Figure 3A:
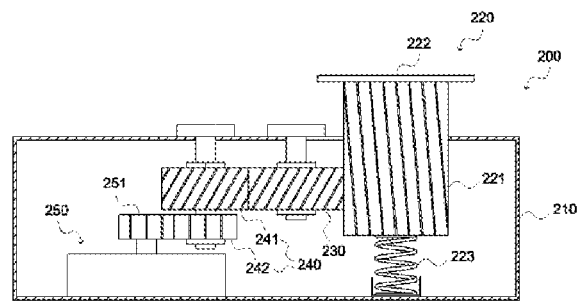
FIGS. 3a and 3b are operation examples of the self power-generation unit.
Figure 3B:
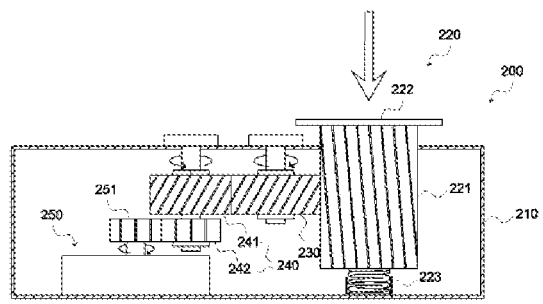

Meanwhile, as shown in FIGS. 3a and 3b, restoring force due to the compression of the spring 223 is generated in the lifting portion 220, and when the outsole 100 is separated from the ground and the pressure is temporarily lost, the compressed spring 223 pushes the lifting portion 220 up to restore the lifting portion 220 to its original state so that the lifting portion 220 may temporarily descend when the pressure is generated again.

When the lifting portion 220 rises and returns to its original position, rotation of the first gear 230 occurs due to the interaction between the screw thread and a screw groove, and the rotation of the second gear 241, the third gear 242, and the fourth gear 251 occurs sequentially, so that all the components that have changed when the lifting portion 220 descends return to their original state.

Therefore, inside the generator 250, power generation by the interaction between the rotating rotor and a stator may repeatedly occur, and the generated electricity may be used to charge the battery 300 provided in the outsole 100.

In addition, as the type of generator 250, any one of a known DC generator or an AC generator may be used, but it is more preferable to use an AC generator with relatively excellent durability, and when the AC generator is used, a diode or bridge circuit for converting the generated alternating current to direct current needs to be additionally provided.

In addition, as described above, the present disclosure may include: the battery 300 which, while being installed in one of the receiving portions, that is, the receiving portion 110b, of the outsole 100, is charged when the self power-generation unit 200 generates power.

In other words, the battery 300 is a secondary battery that can be charged and discharged, and is charged, while being connected to the self power-generation unit 200 through wiring, by a small amount each time the user walks, so that power may be supplied to the multifunction module 400 and the charging port 500 to be described later.

Figure 4:
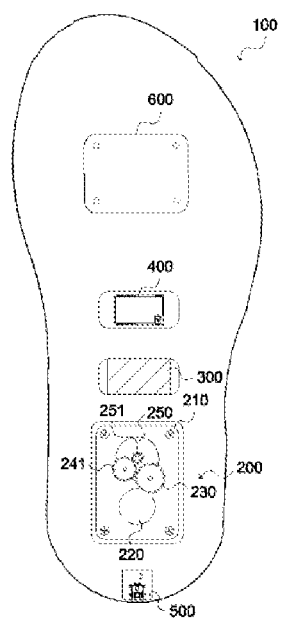
FIG. 4 is a cross-sectional view showing a state in which the self power-generation unit, a battery, a multifunction module, a vibration terminal, and a charging port are installed in the outsole.

To be specific, as shown in FIG. 4, the multifunction module 400 may be installed in one of the receiving portions, that is, the receiving portion 110c, of the outsole 100. The multifunction module 400 includes: GPS that generates location information; a shock sensor that detects the shock that occurs when the user is walking and generates shock information; a posture detection sensor that detects the posture of the shoe and generates posture information; and a communication module that wirelessly transmits the generated location information, shock information, and posture information to a preset user terminal 700.

At this time, as described above, the multifunction module 400 is preferably installed in the receiving portion 110c formed on the middle of the outsole 100, and is connected to the battery 300 through wiring to receive power necessary for operation.

In addition, as shown in FIG. 4, in the outsole 100, the charging port 500 providing electricity charged in the battery 300 to the user terminal 700 through a wired connection may be provided in a form that may be exposed to the outside, and the charging port 500 allows power to be supplied to the user terminal 700 when the wired connection occurs by the user while being connected to the battery 300 through wiring.

The multifunction module 400 is a device provided for the user safety, and generates location information, shock information, and posture information and wirelessly transmits the information to the preset user terminal 700 so that the safety protection function may be performed through analysis of the collected information.

Therefore, the user needs to download and install a dedicated application for the use of the present disclosure in his/her user terminal 700, which is a smartphone, and executes the installed application, registers as a member, and logs in to pair (or interlock) with the multifunction module 400 installed in his/her shoe.

In addition, when the user wears his/her shoe or walks while wearing the shoe, the user terminal 700 may be set to automatically pair with the multifunction module 400 installed in the shoe.

Figure 5:
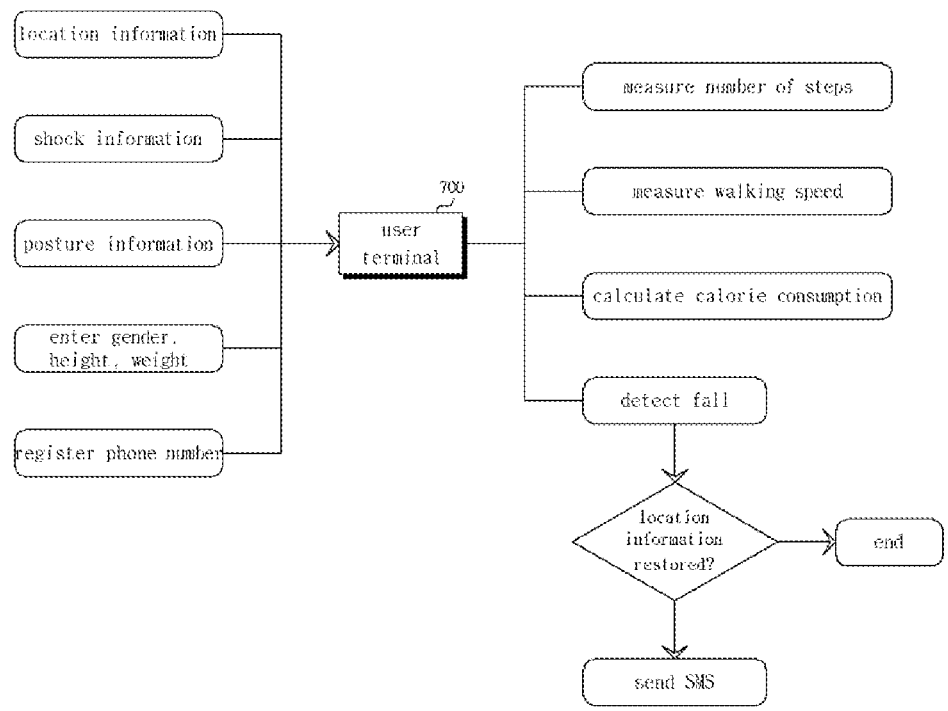
FIG. 5 is an explanatory diagram showing the functions of the present disclosure by the configuration of the multifunction module and a user terminal.

As shown in FIG. 5, in the user terminal 700, the user's number of steps may be measured using shock information among location information, shock information, and posture information transmitted from the multifunction module 400, the user's walking speed may be measured, and calorie consumption may be calculated by reflecting the measured number of steps and walking speed.

In this case, the user may register his/her gender, height, and weight in advance for more accurate calorie consumption calculation.

In addition, in the user terminal 700, a user's fall may be detected using posture information, and shock information may be additionally used to detect a fall.

When the user's fall is detected and the location information is not restored for a predetermined period of time or more, short message (SMS) transmission to a designated phone number by the user terminal 700 may occur, and in the transmitted SMS message, the fact of the user's fall and location information may be included, so that prompt reporting or rescue may be carried out.

Therefore, the user should register in advance one or more phone numbers to which SMS for rescue request is sent, but 119 (equivalent to 911 in the US) may be automatically registered.

Meanwhile, the charging port 500 is a device for supplying power, and a USB terminal for wired connection is provided at the distal end of the charging port 500 so that power may be supplied to the user terminal 700 through a wired connection.

Therefore, the user should have a charging cable for charging the user terminal 700, but considering the hassle and inconvenience of carrying a separate item, one more receiving portions 110 for storing a charging cable may be provided in the outsole 100.

In addition, as shown in FIG. 4, the present disclosure may include the vibration terminal 600 which, while being installed in the receiving portion 110d formed on the front of the outsole 100, vibrates when the user wearing the shoe walks.

The vibration terminal 600 is a non-powered device that vibrates with the vibration generated when the user wearing the shoe walks and the repulsive force of an internal magnet, and transmits vibration to the sole of the user's foot and forms a magnetic field so that effects such as promoting blood circulation and removing dead skin cells may be achieved.

Figure 6A:
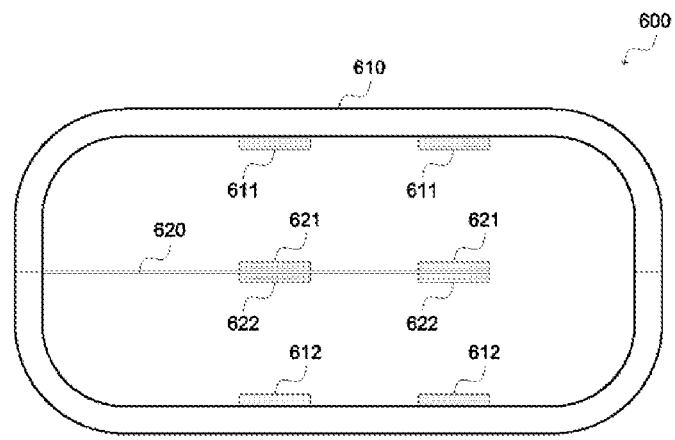
FIG. 6a is a side view showing the internal structure of the vibration terminal.
Figure 6B:
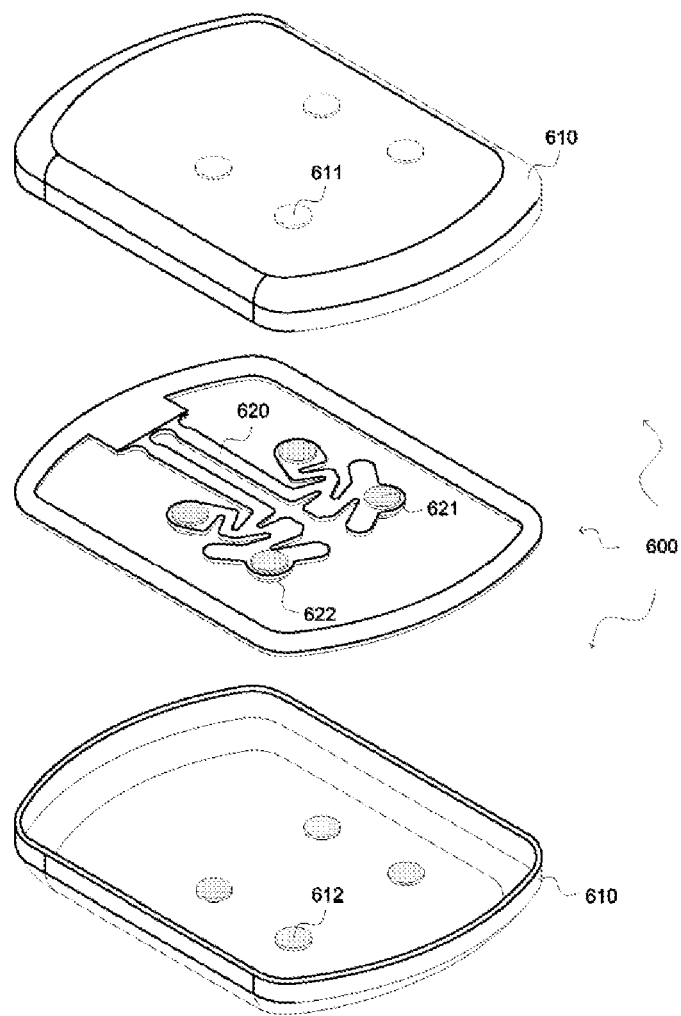
FIG. 6b is an exploded perspective view of the vibration terminal.

To be specific, as shown in FIGS. 6a and 6b, the vibration terminal 600 may include a main body portion 610 in which a space is formed therein, in which a plurality of first stationary magnets 611 is installed on the upper side of the inside of the main body portion 610, and in which a plurality of second stationary magnets 612 is installed in a vertical line with the first stationary magnets 611 on the lower side of the inside of the main body portion 610.

In addition, the vibration terminal 600 may include a vibration plate 620 installed in a form in which one end thereof is fixed between the first stationary magnets 611 and the second stationary magnets 612, and provided with a plurality of first movable magnets 621 that generates a repulsive force in response to the first stationary magnets 611 and a plurality of second movable magnets 622 that generates a repulsive force in response to the second stationary magnets 612 in the main body of the vibration plate 620, so that the vibration plate 620 vibrates due to the vibration generated when the user walks and the repulsive force between the movable magnets 621 and 622 and the stationary magnets 611 and 612.

That is, inside the main body portion 610 constituting the vibration terminal 600, as the vibration plate 620 vibrates due to the vibration generated when the user wearing the shoe walks, a phenomenon in which the distance between the first movable magnets 621 provided in the vibration plate 620 and the first stationary magnets 611 on the upper side of the casing 210 temporarily becomes closer or the distance between the second movable magnets 622 and the second stationary magnets 612 temporarily becomes closer occurs repeatedly.

At this time, between the first movable magnets 621 and the first stationary magnets 611 and between the second movable magnets 622 and the second stationary magnets 612, a repulsive force is generated due to proximity, and the repulsive force generated sequentially and repeatedly at different locations promotes the reciprocating motion of the vibration plate 620, resulting in an increase in the intensity of vibration generated from the vibration terminal 600.

Therefore, the vibration plate 620 is preferably made of a metal material having a high specific gravity and at the same time having a thickness of 0.2 mm or less to be advantageous in generating vibration by reciprocating motion.

The embodiments introduced above are provided as examples so that the technical idea of the present disclosure may be sufficiently conveyed to those skilled in the art to which the present disclosure pertains, and the present disclosure is not limited to the embodiments described above and may be embodied in other forms.

In order to clearly explain the present disclosure, parts not related to the description have been omitted from the drawings, and in the drawings, the width, length, thickness, etc. of components may be exaggerated or reduced for convenience.

In addition, like reference numbers indicate like elements throughout the specification.

INDUSTRIAL APPLICABILITY

According to a self power-generating shoe equipped with a vibrating function and a GPS device of the present disclosure, by installing a self power-generation unit and battery that generate power by pressure on the outsole of the shoe, the battery can be charged while a user wearing the shoe is walking, and by simplifying the configuration and operation method of the self power-generation unit installed in the outsole, it is possible to guarantee sufficient durability, prevent product size expansion, and reduce production costs compared to the conventional cases devised for the same purpose.

The invention claimed is:

1. A self power-generating shoe equipped with a vibrating function and a GPS device, the shoe comprising:
    an outsole (100) constituting a lower portion of the shoe while having a plurality of receiving portions (110) formed therein;
    a self power-generation unit (200) which, while being installed at a heel of the outsole (100), generates power by using pressure generated when a user wearing the shoe walks and a restoring force due to the pressure; and
    a battery (300) which, while being installed in the outsole (100), is charged when the self power-generation unit (200) generates power,
    wherein the self power-generation unit (200) comprises:
    a casing (210) in which a cavity is formed therein;
    a lifting portion (220) configured to include a cylindrical body (221) with a screw thread formed on an outer periphery thereof, an upper head (222) having a wider width than the body (221) and being covered by an insole inside the shoe, and a lower spring (223) supporting the body (221), and move up and down vertically by the pressure and restoring force generated when the user wearing the shoe walks in a state in which the head (222) and a part of the body (221) are installed in the casing (210) in a form protruding outward;
    a first gear (230) axially rotating in a different direction when the lifting portion (220) moves up and down while being installed inside the casing (210) in a form corresponding to the screw thread of the lifting portion (220);
    a gear portion (240) composed of a second gear (241) rotating in correspondence with the first gear (230) and a third gear (242) rotating while connected to the same rotational axis as the second gear (241); and
    a generator (250) having a fourth gear (251), meshing with the third gear (242), installed at an end of a rotating shaft that rotates an internal coil, so that the generator (250) generates power, while being installed inside the casing (210), in conjunction with the third gear (242) that axially rotates,
    wherein the body (221) of the lifting portion (220), the first gear (230), the gear portion (240), and the fourth gear (251) are configured such that their diameters gradually decrease according to a transmission order of power when the lifting portion (220) descends, so that a number of rotations gradually increases, and an amount of power generated by the generator (250) increases as the number of rotations increases,
    wherein the outsole (100) is provided with a multifunction module (400) including:
    the GPS device (not shown) that generates location information;
    a shock sensor (not shown) that detects a shock that occurs when the user is walking and generates shock information;
    a posture detection sensor (not shown) that detects a posture of the shoe and generates posture information; and
    a communication module (not shown) that wirelessly transmits the generated location information, shock information, and posture information to a preset user terminal (700).

2. The shoe of claim 1,
    wherein the user terminal (700) is configured to measure the number of steps the user takes by using the shock information among the location information, shock information, and posture information transmitted from the multifunction module (400), calculate calorie consumption by reflecting the measured number of steps and walking speed, detect a user's fall, and send a short message (SMS) to a designated phone number when the user's fall is detected and the location information is not restored for a predetermined period of time or more.

3. The shoe of claim 1, wherein the outsole (100) is provided with a charging port (500) providing electricity charged in the battery (300) to the user terminal (700) through a wired connection in a form that may be exposed to the outside.

4. The shoe of claim 1, wherein the outsole (100) is provided with a vibration terminal (600) including:
    a main body portion (610) in which a space is formed therein, in which a plurality of first stationary magnets (611) is installed on an upper side of the inside of the main body portion (610), and in which a plurality of second stationary magnets (612) is installed in a vertical line with the first stationary magnets (611) on a lower side of the inside of the main body portion (610); and
    a vibration plate (620) installed in a form in which one end thereof is fixed between the first stationary magnets (611) and the second stationary magnets (612), and provided with a plurality of first movable magnets (621) that generates a repulsive force in response to the first stationary magnets (611) and a plurality of second movable magnets (622) that generates a repulsive force in response to the second stationary magnets (612) in a main body of the vibration plate (620), so that the vibration plate (620) vibrates due to a vibration generated when the user walks and a repulsive force between the movable magnets and the stationary magnets.

* * * * *